United States Patent [19]

Fischer et al.

[11] 4,019,860

[45] Apr. 26, 1977

[54] ANALYTICAL REAGENT FOR CYANIDE

[75] Inventors: Wolfgang Fischer; Renate Linck, both of Darmstadt, Germany

[73] Assignee: Merck Patent Gesellschaft mit beschränkter Haftung, Darmstadt, Germany

[22] Filed: Apr. 5, 1976

[21] Appl. No.: 673,490

[30] Foreign Application Priority Data

Apr. 19, 1975 Germany .......................... 2517483

[52] U.S. Cl. ......................... 23/230 R; 260/240 R
[51] Int. Cl.² ............... C07D 239/22; C09B 57/00; G01N 21/02; G01N 31/00
[58] Field of Search ............... 23/230 R; 260/240 R

[56] References Cited

UNITED STATES PATENTS

| 1,996,630 | 4/1935 | Shonle | 260/257 |
| 2,200,538 | 5/1940 | Bywater | 260/257 |
| 2,678,260 | 5/1954 | Falkof et al. | 23/230 R |
| 2,868,690 | 1/1959 | Martin et al. | 260/257 X |

*Primary Examiner*—Joseph Scovronek
*Attorney, Agent, or Firm*—Millen & White

[57] ABSTRACT

In a method for the determination of cyanide wherein the cyanide is reacted with chloramine-T to form cyanogen chloride, said cyanogen chloride is reacted with pyridine to form glutaconic dialdehyde, and said dialdehyde is reacted with an organic compound to form a colored compound, wherein the improvement comprises employing as said organic compound, N,N'-dialkyl barbituric acid, the alkyl groups being preferably each of 1-6 carbon atoms, and especially N,N'-dimethylbarbituric acid. The latter in a solution of dimethyl sulfoxide has a shelf life of at least one year.

2 Claims, No Drawings

ANALYTICAL REAGENT FOR CYANIDE

BACKGROUND OF THE INVENTION

This invention relates to an analytical reagent suitable for the colorimetric determination of cyanide ions in liquids, and to the production of new colored compounds.

The determination of cyanide has been based on a reaction, known for a long time, wherein cyanide and the active chlorine from chloramine-T (sodium para-toluenesulfonic acid chloramide) are reacted to cyanogen chloride which splits a pyridine ring with the formation of glutaconic dialdehyde. This dialdehyde condenses with two molecules of a suitable organic compound to a colored polymethine compound. Organic compounds which have been recommended for this purpose are barbituric acid [Z. analyt. Chem. [Journal of Analytic Chemistry] 138, 414 [1953]), pyrazolones (Anal. Chem. 19, 272 [1947])], and benzidine ("Deutsche Einheitsverfahren zur Wasseruntersuchung" [German Standard Methods for Water Testing] D 13, 1971, p. 5). These organic compounds have, however, a number of disadvantages which render them essentially useless as a ready-to-use analytical reagent for the detection of cyanide for general purposes, for example, outside of the laboratory.

Specifically, solutions of these organic compounds have a short shelf life: after about two months, barbituric acid in water and pyridine fail to yield exact analytical results, and after about three months, at room temperature, barbituric acid in dimethyl sulfoxide results in sedimentation. (These sediments form in only a few days if the reagent is stored at 42° C.) As for the pyrazolone reagent, it must be prepared fresh daily, since a pink color appears only after two days, and the color of the thus-produced polymethine dye is unstable. Lastly, the benzidine reagent is not only too insensitive, but also carcinogenic.

SUMMARY OF THE INVENTION

One object of this invention is to provide an improved analytical reagent for the determination of cyanide ions, and method for using same. Another object is to provide novel colored compounds which are useful for the determination of cyanide ions. Upon further study of the specification and appended claims, further objects and advantages of this invention will become apparent to those skilled in the art.

To attain these objects, there is provided N,N'-dialkyl-barbituric acid as the key to solving the problems of the prior reagents.

In a comprehensive aspect of this invention, there is provided an analytical reagent for the colorimetric determination of cyanide in liquids, comprising N,N'-dialkyl-barbituric acid, and chloramine-T and pyridine.

Preferably, the N,N'-dialkyl barbituric acid is substituted in the 1,3-position by lower alkyl groups, each being different or preferably the same, such as, for example, methyl, ethyl, propyl, butyl, pentyl, or hexyl groups, especially N,N'-dimethylbarbituric acid. The N,N'-dialkyl-barbituric acid is preferably dissolved in dimethyl sulfoxide as the solvent. Other aprotic solvents such as dimethylformamide, dimethylacetamide, hexamethylphosphoric acid triamide, methylpyrrolidone, tetramethylurea and sulfolane are also suitable but a yellow color appears after several months. It could not be foreseen that, for example, N,N'-dimethylbarbituric acid, as contrasted to barbituric acid, has a shelf life of at least one year in dimethyl sulfoxide, even at a temperature of 42° C. Accordingly, solvent solutions of N,N'-dialkyl-barbituric acid are especially useful per se in the context of this invention. The preferred concentration range of N,N'-dialkyl-barbituric acid is from 3 - 20, especially from 5 - 12% by weight.

The analytical reagent of this invention preferably also contains pH adjusting means, namely bases, acids and/or buffer substances to adjust the pH of the sample solutions to be investigated. For example, the pH value, suitble for the determination, is first adjusted to about 3 and then to 5 in subsequent steps of the reaction. Suitble bases are, for example, alkali metal hydroxides, such as sodium or potassium hydroxide; suitble acids are, for example, mineral acids and carboxylic acids, such as hydrochloric acid, sulfuric acid, tartaric acid, oxalic acid, citric acid, etc. Buffers are, for example, phosphate buffers and EDTA (ethylenediaminetetraacetic acid). EDTA is also utilized for its chelating properties for the elimination of the interfering influence of, for example, copper, zinc, iron(II), and chromium(III) ions.

The preferred weight ratios in the comprehensive analytical reagent including chloramine-T : 1,3-dimethylbarbituric acid : pyridine are 1 : 1 - 10 : 100 - 1000, especially about 1 : 5 : 500. In this connection, it should be kept in mind that pyridine is used not only as a reagent but also as a base for increasing the pH value. If the pH is adjusted by another base, then the amount of pyridine can be reduced by a factor of about 100, so that for example, the range above of 1 : 5 : 500 is reduced to 1 : 5 : 5.

To effect the cyanide determination, the sample solution to be analyzed is first adjusted to a pH of about 2 - 13 with the aid of acids and/or bases. Subsequently, the ready-to-use reagent solutions of chloramine-T, 1,3-dialkyl-barbituric acid, and pyridine are added thereto. After a reaction time of about 5 minutes, the color intensity is measured by conventional techniques, e.g., photometrically at 588 nm. or compared with a calibrated color scale.

The structural formulae of the condensation products of the barbituric acids of the present invention with glutaconic dialdehyde are as follows:

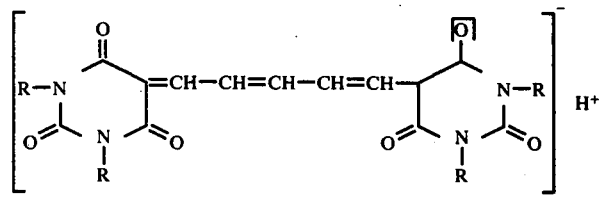

R = alkyl group with up to 6 carbon atoms. All these products are novel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A measuring vessel is rinsed with the sample solution to be tested, having a pH of 2 – 13, and is then filled with 10 ml. of sample solution. Ten drops of a 10% tartaric acid solution and thereafter 10 drops of a 5% EDTA solution are added to the sample solution and the latter is shaken after each addition. Thereafter, 10 drops of a 1% chloramine-T solution are added, the solution is shaken, and then allowed to stand for about 30 seconds. Then, in succession, 5 drops of 10% 1,3-dimethylbarbituric acid solution in dimethyl sulfoxide and 5 drops of pyridine are added and the mixture is shaken after each addition.

After about 5 minutes, the solution containing the thus-produced colored condensation product of glutaconic dialdehyde with 1,3-dimethylbarbituric acid is compared with a color scale or measured photometrically at 588 nm. In this way, a solution is analyzed which contains 0.05 mg. of cyanide ions per liter. The same value is obtained when using a 1.3-dimethylbarbituric acid solution which has been stored for 8 months.

EXAMPLE 2

A self-sufficient, ready-to-use reagent kit contains the following solutions:
1. 10% Tartaric acid solution
2. 5% EDTA solution
3. 1% Chloramine-T solution
4. 10% 1,3-Dimethylbarbituric acid solution in dimethyl sulfoxide
5. Pyridine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method for the colorimetric determination of cyanide in an unknown wherein the cyanide is reacted with chloramine-T to form cyanogen chloride, said cyanogen chloride is reacted with pyridine to form glutaconic dialdehyde, said dialdehyde is reacted with an organic compound to form a colored compound, and the content of cyanide in said solution is determined from the color intensity of said colored compound, wherein the improvement comprises employing as said organic compound, N,N'-dialkyl-barbituric acid, the alkyl groups being each of 1–6 carbon atoms.

2. A method according to claim 1 wherein each alkyl is methyl.

* * * * *